(12) United States Patent
Kinoshita et al.

(10) Patent No.: US 7,753,859 B2
(45) Date of Patent: Jul. 13, 2010

(54) GUIDE WIRE

(75) Inventors: Yasushi Kinoshita, Fujinomiya (JP);
Junichi Kobayashi, Fujinomiya (JP);
Tadashi Kousai, Fujinomiya (JP)

(73) Assignee: Terumo Kabushiki Kaisha,
Shibuya-Ku, Tokyo (JP)

( * ) Notice: Subject to any disclaimer, the term of this patent is extended or adjusted under 35 U.S.C. 154(b) by 0 days.

(21) Appl. No.: 12/116,685

(22) Filed: May 7, 2008

(65) Prior Publication Data

US 2008/0281230 A1    Nov. 13, 2008

Related U.S. Application Data

(60) Provisional application No. 60/917,804, filed on May 14, 2007, provisional application No. 61/006,203, filed on Dec. 31, 2007.

(30) Foreign Application Priority Data

May 11, 2007 (JP) .............................. 2007-127185
Dec. 28, 2007 (JP) .............................. 2007-340859

(51) Int. Cl.
*A61M 25/00* (2006.01)

(52) U.S. Cl. ..................... 600/585; 604/523; 604/526

(58) Field of Classification Search .................. 600/16, 600/585; 604/526, 523
See application file for complete search history.

(56) References Cited

U.S. PATENT DOCUMENTS

| 4,925,445 A | 5/1990 | Sakamoto et al. |
|---|---|---|
| 5,069,226 A | 12/1991 | Yamauchi et al. |
| 5,238,004 A | 8/1993 | Sahatjian et al. |
| 5,269,759 A | 12/1993 | Hernandez et al. |
| 5,368,049 A | 11/1994 | Raman et al. |
| 5,402,799 A | 4/1995 | Colon et al. |
| 5,411,476 A | 5/1995 | Abrams et al. |
| 5,452,726 A | 9/1995 | Burmeister et al. |
| 5,497,786 A | 3/1996 | Urick |
| 5,498,250 A | 3/1996 | Prather |
| 5,772,609 A | 6/1998 | Nguyen et al. |
| 5,797,857 A | 8/1998 | Obitsu |

(Continued)

FOREIGN PATENT DOCUMENTS

EP    1 498 152 A    1/2005

(Continued)

OTHER PUBLICATIONS

Extended Search Report issued in EP Patent Application No. 08 15 5852, Nov. 7, 2008, European Patent Office, The Hague, The Netherlands.

*Primary Examiner*—Adam J Eiseman
(74) *Attorney, Agent, or Firm*—Buchanan Ingersoll & Rooney PC (57) ABSTRACT

A guide wire includes a wire body having a core wire and a resin coating layer covering an outer periphery of a distal section of the wire body, and an annular member provided on the proximal side of the resin coating layer. The outer diameter of the distal end of the annular member and the outer diameter of the proximal end of the resin coating layer are preferably equal, and a distal end face of the annular member is joined to a proximal end face of the resin coating layer.

24 Claims, 7 Drawing Sheets

U.S. PATENT DOCUMENTS

| | | | |
|---|---|---|---|
| 5,876,356 A | 3/1999 | Viera et al. | |
| 5,924,998 A | 7/1999 | Cornelius et al. | |
| 5,951,494 A | 9/1999 | Wang et al. | |
| 6,001,068 A | 12/1999 | Uchino et al. | |
| 6,007,478 A * | 12/1999 | Siess et al. | 600/16 |
| RE36,628 E | 3/2000 | Sagae et al. | |
| 6,093,157 A | 7/2000 | Chandrasekaran | |
| 6,132,389 A | 10/2000 | Cornish et al. | |
| 6,165,292 A | 12/2000 | Abrams et al. | |
| 6,234,981 B1 | 5/2001 | Howland | |
| 6,390,992 B1 | 5/2002 | Morris et al. | |
| 6,520,923 B1 | 2/2003 | Jalisi | |
| 6,673,025 B1 * | 1/2004 | Richardson et al. | 600/585 |
| 6,679,853 B1 | 1/2004 | Jalisi | |
| 6,908,443 B2 * | 6/2005 | Burmeister et al. | 600/585 |
| 7,399,283 B2 * | 7/2008 | Kato | 600/585 |
| 2004/0030266 A1 | 2/2004 | Murayama et al. | |
| 2004/0039308 A1 | 2/2004 | Murayama et al. | |
| 2004/0039309 A1 | 2/2004 | Murayama et al. | |
| 2004/0064069 A1 * | 4/2004 | Reynolds et al. | 600/585 |
| 2005/0038359 A1 | 2/2005 | Aimi et al. | |
| 2005/0152731 A1 | 7/2005 | Mishima et al. | |
| 2006/0235336 A1 | 10/2006 | Tano et al. | |
| 2006/0241419 A1 | 10/2006 | Satou et al. | |
| 2008/0214959 A1 * | 9/2008 | Miyata et al. | 600/585 |

FOREIGN PATENT DOCUMENTS

| | | |
|---|---|---|
| EP | 1 970 092 A | 9/2008 |
| JP | 10-118005 A | 5/1998 |

* cited by examiner

GUIDE WIRE

This application claims priority under 35 U.S.C. §119(e) to U.S. Provisional Application No. 60/917,804 filed on May 14, 2007, and U.S. Provisional Application No. 61/006,203 filed on Dec. 31, 2007, the entire content of both of which is incorporated herein by reference. This application is also based on and claims priority to Japanese Application No. 2007-127185 filed on May 11, 2007 and Japanese Application No. 2007-340859 filed on Dec. 28, 2007, the entire content of both of which is incorporated herein.

TECHNOLOGICAL FIELD

The subject matter disclosed here generally relates to an elongated medical device. More specifically, the subject matter involves a guide wire.

BACKGROUND DISCUSSION

In inserting a catheter into a living body lumen such as a digestive tract and a blood vessel, a guide wire is used to guide the catheter to a target site in the body lumen. The guide wire is used in the state of being inserted in the catheter.

In addition, observation or treatment of a living body lumen or the like by use of an endoscope is also performed, and a guide wire is also used to guide the endoscope or a catheter inserted in the lumen of the endoscope to a target site in the body lumen or the like.

A guide wire of this kind has been proposed in which the guide wire has a resin coating layer at a distal section of a wire body. An example of such a guide wire is disclosed in Japanese Patent Laid-Open No. Hei 10-118005. The resin coating layer makes it possible, in inserting the guide wire into a blood vessel or the like, to prevent the blood vessel wall from being damaged due to contact of the guide wire with the blood vessel wall, whereby safety is enhanced.

In such a conventional guide wire, however, a step is formed between a proximal section of the resin coating layer and the wire body, so that the proximal end part of the resin coating layer may be caught by a medical implement used in combination with the guide wire, specifically the distal end of a catheter or a riser of an endoscope or the like, possibly resulting in exfoliation of the resin coating layer.

In view of this, the proximal section of the resin coating layer has to be tapered so that the proximal end part of the resin coating layer is less likely to be caught by the distal end of the catheter used in combination with the guide wire, or by the riser of the endoscope used in combination with the guide wire.

Examples of the method for the tapering used hitherto include processing by use of a heat-shrinkable tube, physical processing by use of a grinding tool such as a grinder, and chemical processing by use of a solvent.

However, none of these processing methods has made it possible to relatively easily conduct adequate tapering.

In the processing by use of a heat-shrinkable tube, portions other than the portion to be tapered may also be affected by heat and be deformed.

Besides, in the processing by use of a grinding tool such as a grinder, fuzzing may be generated at the ground portion.

Further, in the processing by use of a solvent, it is difficult to control the quantity of the solvent, so that insufficient processing or excessive processing would occur.

SUMMARY

A guide wire comprises a wire body having a core wire. According to one aspect, the guide wire may include a resin coating layer covering an outer periphery of a distal section of the wire body and an annular member provided at the proximal side of the resin coating layer to fill up a step space present between a proximal section of the resin coating layer and the wire body. The outer diameter of the distal end of the annular member and the outer diameter of the proximal end of the resin coating layer are substantially equal, and a distal end face of the annular member is joined to a proximal end face of the resin coating layer. The outer diameter of the annular member may be configured to gradually decrease from the distal side toward the proximal side, and a stepless continuous surface may be formed between the distal end of the annular member and the proximal end of the resin coating layer. The guide wire further may include a stepless continuous surface formed between the wire body and the proximal end of the annular member.

According to various embodiments, the joint surfaces of the annular member and the resin coating layer preferably are formed respectively with a recess and a protrusion for mutual fit. The hardness of the annular member preferably is higher than the hardness of the resin coating layer. The annular member preferably is comprised of a metal or a hard resin. The guide wire preferably includes a coil covering the outer periphery of a distal section of the wire body and formed by helically winding a filament, with the resin coating layer covering the outer periphery of the coil. The coil is wound so that the adjacent turns make contact with each other. The coil preferably is so wound that the filament makes contact with an outer periphery of the wire body. The core wire preferably is provided at the distal end with a flat section having a width larger than the inner diameter of the coil, and the coil is disposed between the flat section and the annular member. The outer surface of a portion, on the distal side relative to the proximal end of the annular member, of the guide wire preferably is coated with a hydrophilic lubricating layer comprised of a hydrophilic material.

According to another aspect, a guide wire comprises a wire, a resin coating layer covering an outer periphery of a distal section of the wire, an annular member provided on the proximal side of the resin coating layer, wherein the outer diameter of the distal end of the annular member and the outer diameter of the proximal end of the resin coating layer are substantially equal, and a distal end face of the annular member is joined to a proximal end face of the resin coating layer. The outer diameter of the annular member preferably gradually decreases from the distal side toward the proximal side, a distal stepless continuous surface is formed between the distal end of the annular member and the proximal end of the resin coating layer, a proximal stepless continuous surface is formed between the wire and the proximal end of the annular member, and the outer surface of a portion of the guide wire on the distal side of the proximal end of the annular member is coated with a hydrophilic lubricating layer.

The coating layer may include an insulating material. The coating layer may include a fluororesin. The annular member preferably is fixed to the wire body by an adhesive or brazing material. The filament preferably includes a tapered section which decreases gradually in outer diameter along the distal direction, and the whole or a part of the annular member is located at the tapered section. The annular member preferably functions to lessen the difference in rigidity between the portion of the wire body on the proximal side relative to the annular member and the portion of the wire body on the distal side relative to the annular member. A distal end face and/or an inner peripheral surface of the annular member preferably can be a roughened surface. The resin coating layer preferably is in secure contact with the outer periphery of a distal section of the core wire. The guide wire further may include a radiopaque marker which is disposed at a distal section of the wire body, the resin coating layer covers an outer periphery of the marker. The guide wire further may include a coil which is disposed so as to cover the outer periphery of a distal section of the wire body and which is formed by helically winding a filament, the resin coating layer covers an outer periphery of the coil. The guide wire further may include a coil which is disposed so as to cover the outer periphery of a distal section of the wire body and which is formed by helically winding a filament and a radiopaque marker which is disposed at a distal section of the wire body on the distal side relative to the coil, the resin coating layer contains radiopaque particles mixed therein, and the resin coating layer covers outer peripheries of the coil and the marker.

The guide wire may satisfy the relationship t≧1.25D, where t is the material thickness of the marker, and D is the outer diameter in cross section of the filament. At least one fixing part for fixing the core wire and the coil preferably is provided on the distal side relative to the annular member. The coil preferably is wound tight so that the adjacent turns thereof make contact with each other. The coil preferably is so wound that the filament makes contact with an outer periphery of the wire. The wire preferably is provided at the distal end thereof with a flat section having a width larger than the inner diameter of the coil, and the coil is disposed between the flat section and the annular member.

According to another aspect, a guide wire comprises a core wire having a distal end section and a proximal end section, and a resin coating layer covering the outer periphery of the distal end section of the core wire. The core wire comprises a distal end section and a proximal end section, with a portion of the core wire between the distal end section and the proximal end section being a tapered section in which the outer diameter of the tapered portion varies and is reduced at a distal part of the tapered portion as compared to a proximal part of the tapered portion. An annular member encircles at least a portion of the tapered section and is positioned entirely on a proximal side of the resin coating layer. The tapered section of the core wire extends distally beyond the distal end of the annular member, and the tapered section of the core wire extends proximally beyond the proximal end of the annular member. The annular member is separate from the resin coating layer and possesses a distalmost end face joined to a proximalmost end face of the resin coating layer. The annular member possesses a thickness that varies along its longitudinal extent, with the thickness of the annular member being less at its proximal end than at its distal end. The outer diameter of the distal end of the annular member is equal to the outer diameter of the proximal end of the resin coating layer.

BRIEF DESCRIPTION OF THE DRAWING FIGURES

FIG. 5(*a*) is a longitudinal cross-sectional view of a guide wire according to a fifth embodiment.

FIG. 5(*b*) is an enlarged longitudinal cross-sectional view of a portion of a further embodiment of the guide wire.

FIG. 6(*a*) is a longitudinal cross-sectional view of a guide wire according to a fifth embodiment.

FIG. 6(*b*) is an enlarged longitudinal cross-sectional view of a portion of a further embodiment of the guide wire.

DETAILED DESCRIPTION

Figure 1:
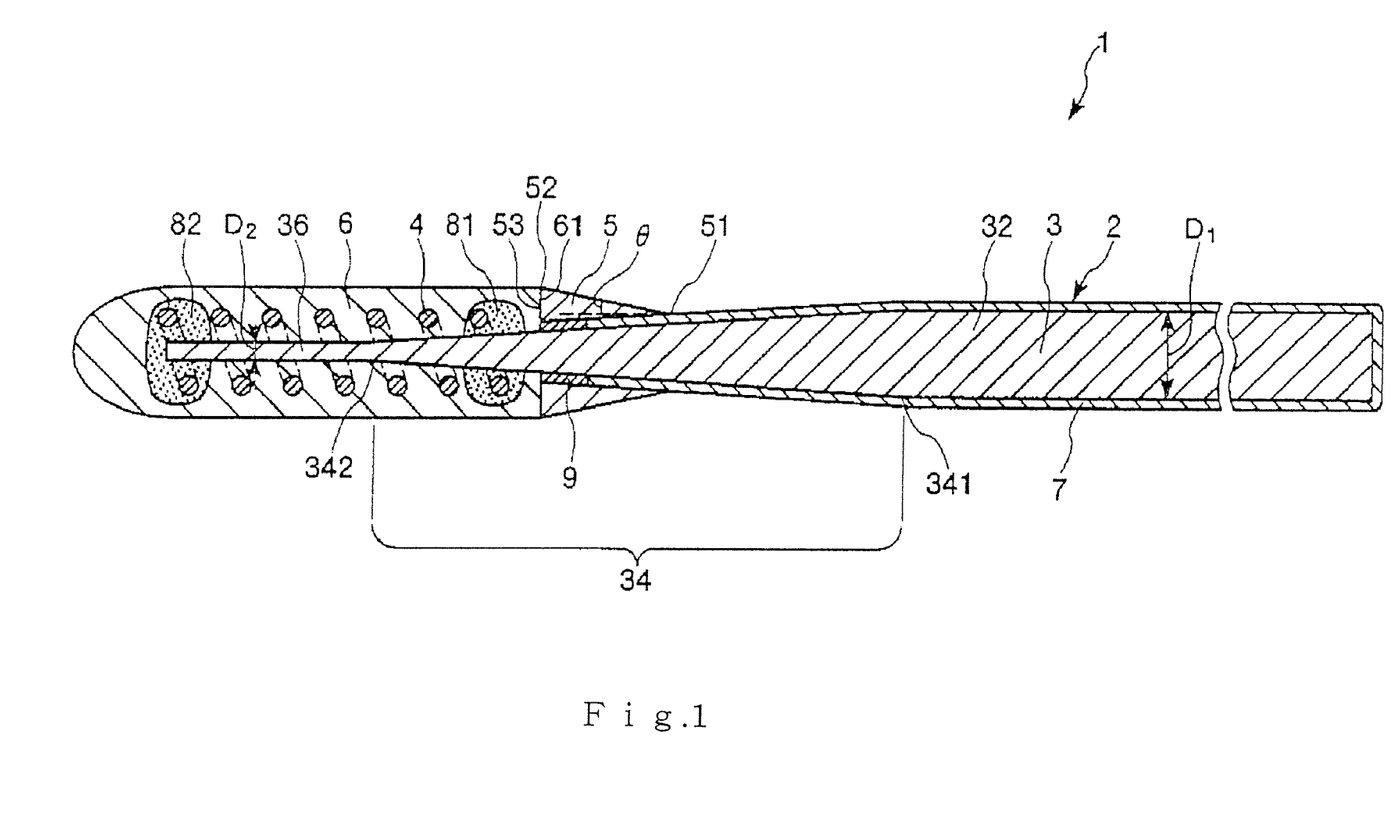
FIG. 1 is a longitudinal cross-sectional view of a first embodiment of the guide wire disclosed herein.

FIG. 1 illustrates a guide wire according to one embodiment. To help facilitate an understanding, the illustration in FIG. 1 depicts the guide wire shortened in the longitudinal direction and exaggerated in the diametrical direction (thickness direction). Thus, the ratio between the illustrated size in the longitudinal direction and the illustrated size in the diametrical direction differs from the actual ratio.

The guide wire 1 shown in FIG. 1 is a catheter guide wire used in a manner in which it is inserted in the lumen of a catheter (inclusive of endoscope). The guide wire includes: a wire body 2 comprised of a flexible or elastic member (for example a core wire) and a proximal side coating layer (hereinafter referred to simply as "coating layer") 7; a helical coil 4; a resin coating layer 6; and an annular member 5.

In the present embodiment, the wire body 2 includes a single continuous core wire 3 and the coating layer 7. The core wire 3 and the wire body 2 are circular in cross-sectional shape. It is to be noted though that the core wire 3 and the wire body 2 are not limited to this cross-sectional shape or the particular configuration shown in FIG. 1. For example, the core wire 3 may be comprised of a plurality of core wires of the same material or different materials that are joined to each other by, for example, welding or brazing or the like. In addition, the wire body 2 may have other components (for example, another layer or the like), and the coating layer 7 may be omitted. Where the core wire 3 is formed by joining two core wires, for example, the joint part may be located at any of a body section 32, a tapered section 34, and a small diameter section 36 of the core wire which will be described below.

The overall length of the guide wire 1 is not limited to a particular length. However, a preferable length for the guide wire is about 200 to 5000 mm. The outer diameter of the guide wire 1 can also be of various dimensions, though is preferably about 0.2 to 1.2 mm.

The core wire 3 extends over substantially the entire length of the guide wire 1, and includes the body section 32 corresponding to a body section of the guide wire 1, the tapered section 34 located on the distal side of the body section 32, and the small diameter section 36 located on the distal side of the tire tapered section 34. The body section 32 is substantially uniform in outer diameter, the tapered section 34 gradually decreases in outer diameter along the distal direction, and the small diameter section 36 is substantially uniform in outer diameter.

With the core wire 3 provided with the tapered section 34, the elasticity of the core wire 3 gradually or continuously increases along the distal direction from a position near the boundary part between the body section 32 and the tapered section 34 (e.g., tapered section proximal end 341), resulting in the elasticity of the guide wire 1 being increased, so that the steerability and safety at the time of inserting the guide wire 1 into a living body are enhanced.

The small diameter section 36 provided on the distal side of the tapered section 34 contributes to making the distalmost elastic part relatively long, with the result that the distalmost part is more elastic.

At least a part of the small diameter section 36 of the core wire 3 may be a reshapable section which can be reshaped. The reshapable section preferably has a flat plate-like shape, a polygonal-base columnar shape or a similar shape.

The outer diameter D1 of the body section 32 of the core wire 3 (i.e., the outer diameter of the tapered section proximal end 341) is not limited to a particular value, though is preferably about 0.3 to 1.0 mm, more preferably about 0.4 to 0.7 mm.

Also, the outer diameter D2 of the small diameter section 36 of the core wire 3 (i.e., the outer diameter of the tapered section distal end 342) is not particularly limited, though is preferably about 0.05 to 0.3 mm, more preferably about 0.1 to 0.2 mm. The outer diameter of the small diameter section 36 need not necessarily be uniform. Indeed, the outer diameter of the small diameter section 36 may gradually decrease toward the distal end.

The length of the tapered section 34 can vary depending on, for example, the use of the guide wire 1 and the kind of guide wire 1. A preferable for the tapered section 34 is about 10 to 300 mm, more preferably 30 to 250 mm.

The length of the small diameter section 36, though not limited to a particular value, is preferably about 0 to 100 mm, more preferably about 10 to 50 mm.

The taper angle of the tapered section 34 may be uniform along the longitudinal direction of the core wire 3 as illustrated, or may vary along the longitudinal direction in some part(s) of the tapered section 34. The tapered section 34 is not limited to being located at one position. That is, tapered sections may be provided at two or more positions/locations along the length of the guide wire.

Examples of the material constituting the core wire 3 include metallic materials such as stainless steel, Ni—Ti alloys, Ni—Al alloys, Cu—Zn alloys and the like superelastic alloys, and resin materials comparatively high in rigidity. These materials may be used either singly or in combinations of two or more.

The coil 4 is disposed around the outer periphery of the distal section of the core wire 3. More specifically, in the embodiment shown in FIG. 1, the coil 4 is disposed around the outer periphery of the small diameter part 36 of the core wire 3 and around the outer periphery of a portion of the tapered section 34 ranging from the distal end of the tapered section to an intermediate position. The coil 4 is a helical member formed by helically winding a filament, and is disposed to cover the outer periphery of a distal-side part of the core wire 3. In the arrangement shown in FIG. 1, the distal-side part of the core wire 3 is positioned in the central part (inclusive of substantially central) of the inside of the coil 4, meaning that the distal side part of the core wire 3 is coaxial with the coil 4. The distal-side part of the core wire 3 is positioned relative to the coil 4 so that the distal-side part of the core wire 3 does not make contact with the inside surface of the coil 4. Namely, the inner surface of the filament of the coil 4 is spaced from the outer periphery of the core wire 3. In addition, the proximal end of the coil 4 is located at an intermediate part of the tapered section 34 of the core wire 3 between the tapered section distal end 342 and the tapered section proximal end 341.

Variations on the above described spaced arrangement of the coil 4 and the core wire 3 are possible. In this regard, the coil 4 may be wound so that the filament makes contact with the outer periphery of the core wire 3, as in further embodiments which will be described later.

In the configuration shown in FIG. 1, a gap exists between the adjacent turns of the helically wound filament in the condition where no external force is exerted on the coil 4. However, the adjacent turns of the helically wound filament may be disposed with no gap therebetween in the condition where no external force is applied to the coil 4. The coil 4 may be wound tight so that the adjacent turns of the filament make contact with each other.

The coil 4 is preferably made of a metallic material. Examples of the metallic material constituting the coil 4 include stainless steel, superelastic alloys, cobalt alloys, noble metals such as gold, platinum and tungsten and their alloys (e.g., platinum-iridium alloy). Especially where the coil 4 includes a radiopaque material such as a noble metal, the guide wire 1 acquires a radioscopically visible property, which is preferable because the guide wire 1 can be inserted into a living body while checking or visualizing the position of its distal section under radioscopic observation. In addition, the coil 4 may have a distal-side section and a proximal-side section made of different materials. For example, a configuration may be adopted in which the distal-side section of the coil 4 is a coil portion made of a radiopaque material and the proximal-side section of the coil 4 is a coil portion made of a comparatively radiolucent material (stainless steel or the like). The overall length of the coil 4 is not necessarily limited, but is preferably about 5 to 500 mm.

The proximal section and the distal section of the coil 4 are fixed, preferably firmly attached, to the core wire 3 through fixing materials 81, 82, respectively.

These fixing materials 81, 82, or two fixing parts for fixing the core wire 3 and the coil 4 to each other, are provided on the distal side relative to an annular member 5 to be described later. The fixing materials 81, 82 are out of contact with the annular member 5. This makes it possible to prevent electrical conduction between the core wire 3 and the annular member 5 through the fixing material 81, and to prevent electrical conduction between the outer surface of the guide wire and the core wire 3.

The fixing materials 81, 82 can be a solder material or a brazing material. Alternatively, the fixing materials 81, 82 can be an adhesive, for example. In addition, the method of fixing the coil 4 relative to the core wire 3 is not limited to the use of the fixing material(s) 81, 82. For example, welding can be employed to fix the coil 4 relative to the wire body. To avoid damaging the inside wall of a body lumen such as a blood vessel, the distal end surface of the fixing material 82 preferably possesses a rounded shape.

While the filament is circular in cross-sectional shape in the present embodiment, the cross-sectional shape of the filament may be, for example, an ellipse, a tetragon (especially a rectangle) or other shapes.

The resin coating layer 6 of the guide wire 1 covers the outer peripheries or outer surfaces of the distal section of the core wire 3, the coil 4, and the fixing materials 81, 82. The resin coating layer 6 is securely adhered to the outer periphery of the distal section of the core wire 3.

The resin coating layer 6, in addition to covering the outer surface of the coil 4, also extends inside the coil 4 in the illustrated embodiment. Alternatively, the resin coating layer 6 may be configured so that it does not enter inside the coil 4.

The resin coating layer 6 may be formed for any of various purposes. For example, the resin coating layer 6 may be provided for the purpose of enhancing safety at the time of inserting the guide wire 1 into a blood vessel or the like. For this purpose, the resin coating layer 6 preferably includes a material relatively rich in elasticity. It is particularly preferable that the resin coating layer 6 includes a material which is more elastic than the coating layer 7, the latter of which will be described in more detail below.

Examples of materials rich in elasticity include polyolefins such as polyethylene and polypropylene, polyvinyl chloride, polyesters (PET, PBT, etc.), polyamides, polyimides, polyurethane, polystyrene, silicone resins, thermoplastic elastomers such as polyurethane elastomer, polyester elastomers and polyamide elastomers, various rubber materials such as latex rubber and silicone rubbers, and composite materials obtained by combining two or more of these materials.

Particularly, where the resin coating layer 6 includes one or some of the thermoplastic elastomers and the various rubber materials, the distal section of the guide wire 1 exhibits enhanced elasticity, so that it is possible to more securely prevent the guide wire 1 from damaging the inside wall of a blood vessel or the like when inserted into the blood vessel or the like, and extremely high safety is attained.

Particles including a radiopaque material are preferably dispersed in the resin coating layer 6. This helps ensure that the guide wire 1 acquires a radioscopically visible property. In this way, the position of the guide wire 1 inserted into a living body, more specifically the position of the distal end of the guide wire, can be visually observed and checked under radioscopic observation.

The material constituting the particles is not particularly limited insofar as it is a radiopaque material. Examples of the radiopaque material include noble metals such as platinum, tungsten, etc. and their alloys (e.g., platinum-iridium alloy).

The thickness of the resin coating layer 6 is not limited, and is preferably appropriately selected depending upon the purpose of the resin coating layer 6, the material constituting the layer 6, the method of forming the layer 6, and other relevant considerations. Ordinarily, the thickness of then resin coating layer 6 is preferably about 100 to 500 µm, more preferably about 150 to 350 µm. If the thickness of the resin coating layer 6 is too small, the purpose of the resin coating layer 6 may be exhibited insufficiently. On the other hand, when the thickness of the resin coating layer 6 is too large, the layer 6 may affect the physical properties of the wire body 2.

The resin coating layer 6 may be a laminate of two or more layers.

The wire body 2 also has the coating layer 7 which covers the outer periphery of the core wire 3 on the proximal side relative to the resin coating layer 6. The distal end of the coating layer 7 and the proximal end of the resin coating layer 6 are axially spaced apart from one another by a predetermined distance and are not in contact with each other.

The coating layer 7 may be formed for any of a variety of purposes. An example of one purpose to be served by the coating layer 7 is to reduce friction, and enhance the slidability, of the guide wire 1, thereby enhancing the operational characteristics of the guide wire 1.

To reduce the friction of the guide wire 1, the coating layer 7 preferably includes a material which can reduce the friction as will be described later. This ensures that the frictional resistance on the inside wall of a catheter used together with the guide wire 1 is reduced, the slidability is enhanced, and the operationality of the guide wire 1 in the catheter will be better. In addition, with the sliding resistance of the guide wire 1 thus lowered, it is possible to more securely prevent the guide wire 1 from kinking or twisted when the guide wire 1 is moved and/or rotated inside a catheter.

The coating layer 7 preferably includes or is made from an insulating material. Since the annular member 5 is positioned around the outer periphery of a portion of the coating layer 7, the core wire 3 and the annular member 5 can be insulated from each other by forming the coating layer 7 from an insulating material. This helps ensure that, for example in the case where a medical implement used by passing an electric current is disposed along the guide wire 1, leakage of current from the outer surface of the annular member 5 and the related trouble can be prevented from occurring.

Examples of the insulating material capable of reducing the friction include polyolefins such as polyethylene and polypropylene, polyvinyl chloride, polyesters (PET, PBT, etc.), polyamides, polyimides, polyurethane, polystyrene, polycarbonate, silicone resins, fluororesins (PTFE, ETFE, PFA, etc.), and their composite materials.

Where a fluororesin (or a composite material containing a fluororesin) among the above-mentioned insulating materials is used, it is possible to more effectively lower the frictional resistance, and enhance slidability, between the guide wire 1 and a catheter, so that the operationality of the guide wire 1 inside the catheter will be better. In addition, this makes it possible to more securely prevent the guide wire 1 from kinking (sharp bending) or twisting when the guide wire 1 is moved and/or rotated inside a catheter.

Besides, where a fluororesin (or a composite material containing the same) is used, coating the core wire 3 with the resin material can be performed in the condition where the resin material is heated, by a method such as baking and spraying. This promises a remarkable adhesion between the core wire 3 and the coating layer 7.

In addition, where the coating layer 7 includes a silicone resin (or a composite material containing the same), the coating layer 7 adhered to the core wire 3 assuredly and firmly can be formed without need for heating, at the time of forming the coating layer 7. Specifically, where the coating layer 7 includes a silicone resin (or a composite material containing the same), a reaction-curing type material or the like can be used, so that the formation of the coating layer 7 can be carried out at room temperature. With the coating layer 7 thus formed at room temperature, the coating can be carried out easily.

The thickness of the coating layer 7 is not limited to a particular thickness. The thickness of the coating layer 7 is appropriately selected in consideration of the purpose of the coating layer 7, the material constituting the coating layer 7, the method of forming the coating layer 7 and other relevant considerations. Ordinarily, the thickness is preferably about 1 to 100 µm, more preferably about 1 to 30 µm. If the thickness of the coating layer 7 is too small, the purpose of the coating layer 7 may not be sufficiently exhibited, and exfoliation of the coating layer 7 may occur. On the other hand, when the thickness of the coating layer 7 is too large, the coating layer 7 may affect the physical properties of the wire body 2, and exfoliation of the coating layer 7 may occur. The coating layer 7 may be a laminate of two or more layers.

In the guide wire 1 here, the outer peripheral surface of the core wire 3 may be subjected to a treatment (e.g., surface roughening, chemical treatment, heat treatment, etc.) for enhancing the adhesion between the resin coating layer 6 and the coating layer 7. Alternatively, an intermediate layer capable of enhancing the adhesion between the resin coating layer 6 and the coating layer 7 may be provided.

The annular member 5 is located and configured to fill up the step space present between the proximal part of the resin coating layer 6 and the wire body 2. That is, the outer diameter of the proximal end of the resin coating layer 6 is greater than the outer diameter of the portion of the wire body 2 immediately adjoining the proximal end of the resin coating layer 6, and this difference between the outer diameter of the proximal end of the resin coating layer 6 and the outer diameter of the portion of the wire body 2 immediately adjoining the proximal end of the resin coating layer forms a step-shaped space in which is positioned the annular member 5. The annular member 5 is provided around the outer periphery of the coating layer 7, particularly the outer periphery of the distal end portion of the coating layer 7. The annular member 5 is in secure contact with the outer periphery of the coating layer 7.

The outer diameter of the proximal end of the resin coating layer 6 is larger than the outer diameter of the core wire 3 at a point along the length of the guide wire corresponding to the proximal end of the resin coating layer 6, and the stepped space arises from this difference in outer diameter. That is, the outer diameter of the proximal end of the resin coating layer 6 and the outer diameter of the portion of the core wire 3 immediately adjoining the proximal end of the resin coating layer forms a step-shaped space.

The outer diameter of the distal end 52 of the annular member 5 is equal (inclusive of approximately or substantially equal) the outer diameter of the proximal end of the resin coating layer 6. Additionally, the distal end face 53 of the annular member 5 is joined to the proximal end face 61 of the resin coating layer 6. The distal end face 53 of the annular member 5 is preferably adhered to the proximal end face 61 of the resin coating layer 6. In this case, the resin coating layer 6 is prevented from extending proximally beyond the distal end 52 of the annular member 5 to partly cover the annular member 5. In other words, a stepless continuous surface is formed between the distal end 52 of the annular member 5 and the proximal end of the resin coating layer 6.

The outer diameter of the annular member 5 gradually decreases from the distal side toward the proximal side extending in the proximal direction, with the outer diameter of the annular member 5 being smaller at the proximal end 51 than at the distal end 52. In addition, the outer diameter of the proximal end 51 of the annular member 5 is equal (inclusive of approximately or substantially equal) to the outer diameter of the wire body 2 at the proximal end 51 of the annular member 5. In other words, a stepless continuous surface is formed between the wire body 2 and the proximal end 51 of the annular member 5. The outer diameter of the proximal end 51 of the annular member 5 is smaller than the outer diameter of the body section 32 of the core wire 3. The proximal end 51 of the annular member 5 is located on the distal side relative to the proximal end 341 of the tapered section 34. The annular member 5 preferably has a length of 0.5 to 15 mm.

The inner diameter of the annular member 5 is greater at the proximal end 51 than at the distal end 52. This is because the annular member 5 is located on the tapered section 34 of the core wire 3. That is, the inner periphery of the annular member possesses a taper that closely matches the taper of the tapered section 34 (i.e., the inner periphery of the annular member 5 is parallel to the out periphery of the tapered section along the portion of the guide wire at which the annular member 5 and the tapered section 34 longitudinally overlap).

Of course, as an alternative, the inner diameter of the proximal end 51 may be equal to the inner diameter of the distal end 52. In this alternative, the inner periphery of the proximal end 51 would be in secure contact with the coating layer 7, and a space would exist between the inner periphery at the distal end 52 and the coating layer 7 (or the core wire 3), but the annular member 5 can be fixed to the core wire 3 by filling up the space with a fixing material 9 which will be described later.

This annular member 5 makes it possible to inhibit or prevent the proximal end part of the resin coating layer 6 from being caught by or on a medical implement used in combination with the guide wire 1, specifically the distal end of a catheter or a riser of an endoscope or the like. The annular member also helps prevent the resin coating layer 6 from being exfoliated due to such catching. In addition, it is possible to prevent the slidability of the guide wire 1 from being lowered due to the step.

The inclination angle θ of the annular member 5, in the present embodiment, is uniform along the longitudinal direction of the core wire 3. However, the inclination angle θ may be varied at some portion(s) in the longitudinal direction.

The inclination angle is preferably not more than 30°, more preferably about 2 to 25°, and further preferably about 5 to 20°. This makes it possible to prevent the annular member 5 from being caught by or on a medical implement used in combination with the guide wire 1, specifically the distal end of a catheter or a riser of an endoscope or the like.

The length of the annular member 5 is preferably greater than the outer diameter of the distal end 52 of the annular member 5. Particularly, the length of the annular member 5 is preferably two to five times the outer diameter of the distal end 52.

The hardness of the annular member 5 is set to be higher than (greater than) the hardness of the resin coating layer 6. This makes it possible to prevent the annular member 5 from being caught by a medical implement used in combination with the guide wire 1, specifically the distal end of a catheter or a riser of an endoscope or the like.

Either one or both of the distal end face 53 and the inner peripheral surface of the annular member 5 may be a roughened surface. When the distal end face 53 of the annular member 5 is a roughened surface, its adhesion to the resin coating layer 6 is enhanced. In a somewhat similar manner, when the inner peripheral surface of the annular member 5 is a roughened surface, its adhesion to the coating layer 7 and the fixing material 9 (described later) is enhanced.

In addition, the material constituting the annular member 5 is not particularly limited. Various resin materials, various metallic materials and the like can be used. For example, the same material as that of the resin coating layer 6 can be used, and a material different from that of the resin coating layer 6 can also be used.

It is to be noted, however, that the annular member 5 preferably includes a metallic material or a hard resin material, particularly, a metallic material.

Examples of the hard resin material which can be used to fabricate the annular member 5 include polycarbonate, polyamides, polyethylene terephthalate, polyacetal, and polyphenylene sulfide.

Examples of the metallic material which can be used to constitute the annular member 5 include stainless steel, titanium, titanium alloys, Ni—Ti alloy, aluminum, gold, and platinum. When the annular member 5 includes a noble metal such as gold and platinum or an alloy thereof, the radioscopically visible property is enhanced.

Where the annular member 5 includes a metallic material, the outer periphery of the annular member 5 may be covered with a coating layer (not shown). The material constituting the coating layer is not limited to a particular material. Examples include various resin materials, various ceramics, various metallic materials and the like can be used. It is particularly preferable to use an insulating material.

The annular member 5 is firmly attached to the core wire 3 by the fixing material 9 provided on the outer periphery of the core wire 3, at a position between the proximal end of the resin coating layer 6 and the distal end portion of the coating layer 7.

The fixing material 9 preferably includes an adhesive, particularly an insulating adhesive. This helps ensure that the core wire 3 and the annular member 5 can be insulated from each other, and, for example where a medical implement used by passing an electric current is disposed along the guide wire 1, leakage of current from the outer surface of the annular member 5 and similar troubles can be avoided or prevented from occurring.

The fixing material 9 is not limited to an adhesive. For example, where the annular member 5 includes a metallic material, the fixing material 9 may be a solder material or a brazing material. In addition, the method of fixing the annular member 5 is naturally not limited to the use of a fixing material.

The annular member 5 is located at the tapered section 34 of the core wire 3. While the whole part of the annular member 5 is located at the tapered section 34 in the illustrated embodiment shown in FIG. 1 (i.e., the tapered section extends in the distal direction beyond the distal end of the annular member 5, and extends in the proximal direction beyond the proximal end of the annular member 5), variations on this arrangement are possible. A configuration may be adopted in which only a part of the annular member 5 is located at the tapered section 34.

The annular member 5 moderates the difference in rigidity (e.g., flexural rigidity, torsional rigidity) between the portion of the wire body 2 on the proximal side of the annular member 5, and the portion of the wire body 2 on the distal side of the annular member 5. Specifically, as mentioned above, at the tapered section 34 of the core wire 3, the outer diameter gradually decreases along the distal direction, and the rigidity is gradually lowered along the distal direction. On the other hand, the resin coating layer 6 is provided on the wire body 2 on the distal side of the annular member 5. In the absence of the annular member 5, the rigidity is abruptly increased at the proximal end of the resin coating layer 6, which leads to a higher possibility of kinking at the proximal end. However, in the guide wire 1 in the present embodiment, the presence of the annular member 5 helps ensure that an abrupt increase in rigidity at the proximal end of the resin coating layer 6 is avoided, and any associated kinking at the proximal end of the resin coating layer 6 is not as likely to occur, preferably is prevented from occurring.

One example of a method of manufacturing the guide wire 1 described above is set forth below.

First, beginning with the wire body 2 in which the outer periphery of the core wire 3 is covered with the coating layer 7, the coil 4 is fixed to the distal section of the wire body 2. The coil 4 is fixed by the fixing materials 81, 82, and the annular member 5 is fixed to the proximal side of the coil 4 by the fixing material 9. The fixation of the coil 4 and the fixation of the annular member 5 may be conducted in any order.

Next, the outer peripheries of the distal section of the wire body 2, the coil 4, and the fixing materials 81, 82 are covered with the resin coating layer 6.

Then, in a situation in which, for example, the proximal end of the resin coating layer 6 is raised relative to the distal end 52 of the annular member 5 so that a step exists between the resin coating layer 6 and the annular member 5, the resin coating layer 6 is ground or scraped to form a smooth continuous surface at the boundary of the annular member 5 and the resin coating layer 6. The purpose is to equalize the outer diameter of the proximal end of the resin coating layer 6 and the outer diameter of the distal end 52 of the annular member 5.

As another example, in a situation when the resin coating layer 6 extends proximally beyond the distal end 52 of the annular member 5 to partly cover (overlap) the annular member 5, the resin coating layer 6 at the overlapping portion is ground or scraped away so that the resin coating layer 6 will not cover or overlap with the annular member 5.

As described above, the guide wire 1 disclosed here, with the inclusion of the annular member 5, is not so susceptible to the proximal end part of the resin coating layer 5 being caught by a medical implement used in combination with the guide wire 1, specifically the distal end of a catheter or a riser of an endoscope or the like. The annular member 5 also helps prevent the resin coating layer 6 from being exfoliated due to such catching. In addition, it is possible to inhibit or prevent the slidability of the guide wire 1 from being lowered due to the step.

The results mentioned above can be developed by only providing the annular member 5, without the need for tapering the proximal part of the resin coating layer 6. Thus, the guide wire 1 here can be manufactured more easily.

Figure 2:
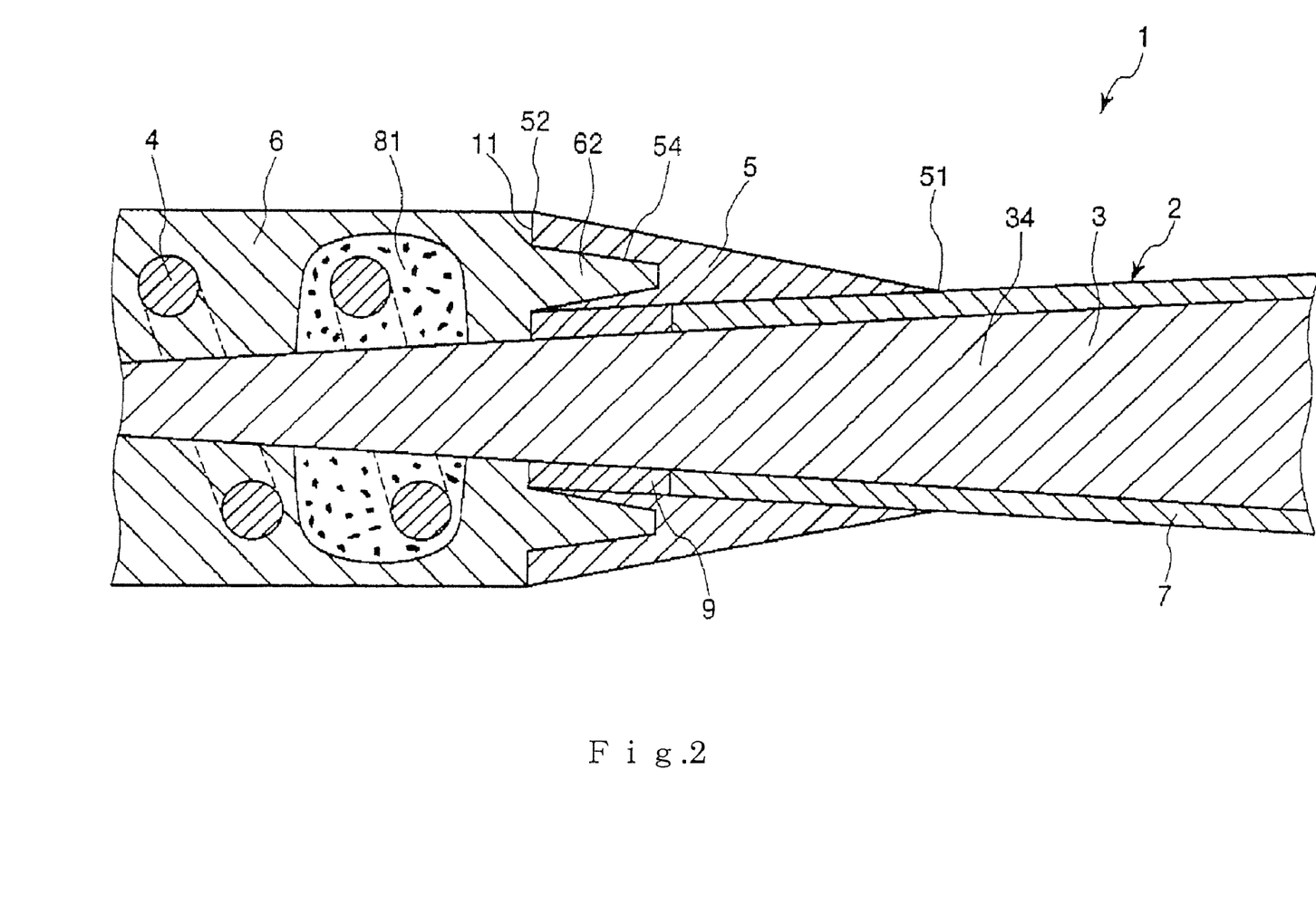
FIG. 2 is an enlarged longitudinal cross-sectional view of a portion of a guide wire according to a second embodiment.

FIG. 2 illustrates a portion of a guide wire according to a second embodiment.

The following description centers primarily on the difference(s) between this embodiment and the embodiment described above. Features associated with this second embodiment of the guide wire that are the same as those associated with the first embodiment are identified by common reference numerals, and a detailed description of such features is not repeated.

As shown in FIG. 2, in the guide wire 1 of the second embodiment, the joint surface 11 of the annular member 5 and the resin coating layer 6 are provided with a recess and a protrusion for effecting a mutual fit. In the illustrated embodiment, the annular member 5 is formed with a groove 54 (axially extending groove or recess), and the resin coating layer 6 is formed with a rib or protrusion 62 (axially extending protrusion or rib), and the protrusion 62 is inserted into the groove 54, resulting in the mutual fit. Both the protrusion (rib) 62 and the recess (groove) 54 are annular in form.

The rib or protrusion 62 of the resin coating layer 6 is formed by filling the groove or recess 54 of the annular member 5 with the constituent material of the resin coating layer 6, at the time of covering the outer peripheries of a distal section of a wire body 2, a coil 4, and fixing materials 81, 82 with the resin coating layer 6.

The guide wire 1 according to this second embodiment possesses the same desirable attributes as those discussed above in connection with the first embodiment.

In addition, in this second embodiment of the guide wire 1, cracking at the joint surface 11 between the annular member 5 and the resin coating layer 6 is not as likely to occur. Particularly, cracking at the joint surface 11 upon bending or curving of the guide wire 1 can be avoided or prevented from occurring.

The configuration of the joint surface shown in FIG. 2 can also be applied to other versions of the guide wire such as the embodiments of the guide wire shown in FIGS. 3 and 4 which are described below.

Figure 3:
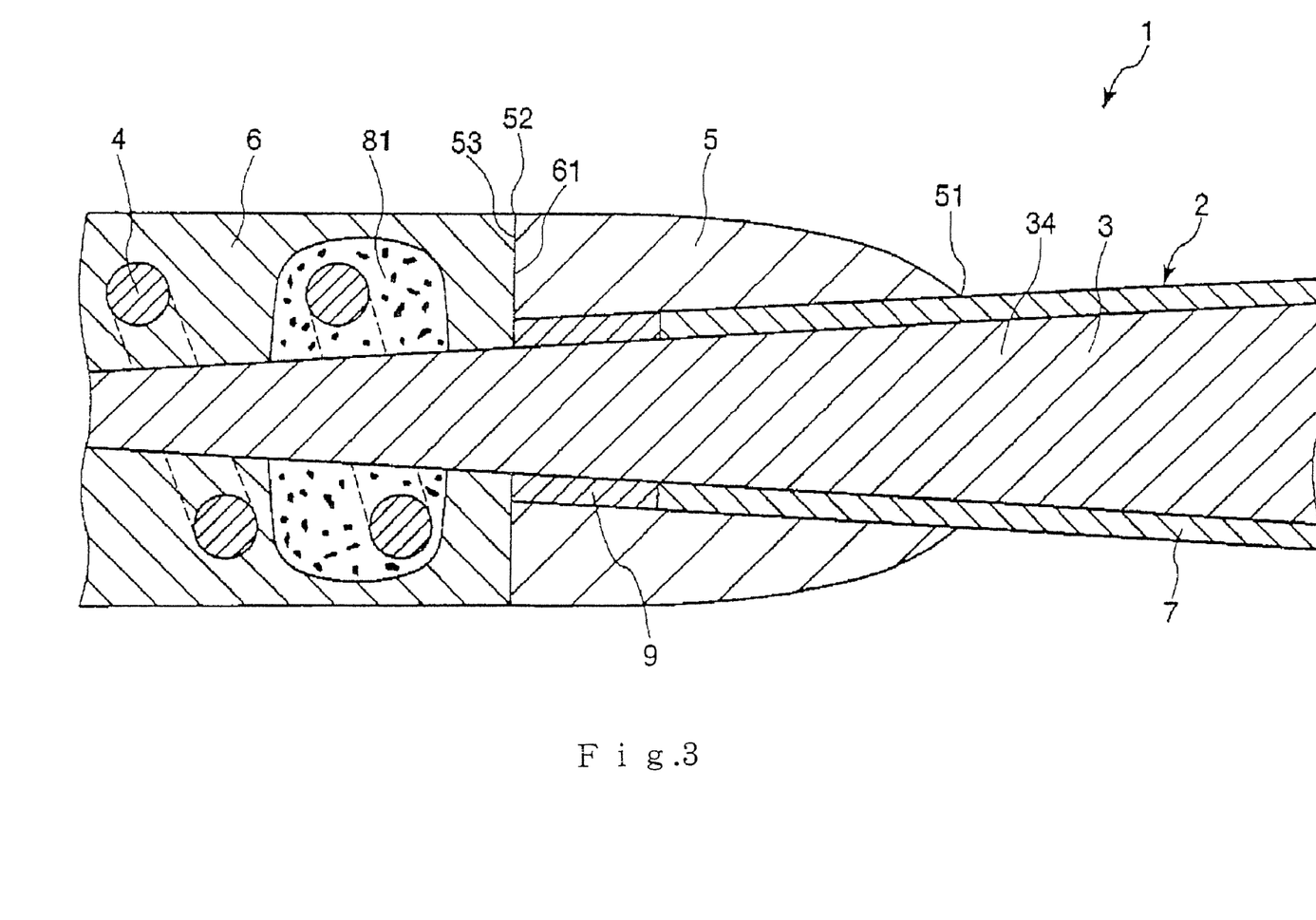
FIG. 3 is an enlarged longitudinal cross-sectional view of a portion of a guide wire according to a third embodiment.

FIG. 3 is a longitudinal cross-sectional view of a portion of a guide wire according to a third embodiment. The following description centers primarily on the difference(s) between this third embodiment and the embodiments described above. Features associated with this third embodiment of the guide wire that are the same as those associated with embodiments described above are identified by common reference numerals, and a detailed description of such features is not repeated.

FIG. 3 shows that the guide wire 1 of the third embodiment includes an annular member 5 whose inclination angle (the angle of inclination of the outer surface of the annular member 5) varies along the longitudinal direction of the core wire 3. In the illustrated embodiment, the inclination angle of the annular member 5 gradually increases in the proximal direction. As illustrated, the outer surface of the annular member 5 is curved, specifically, convex. The guide wire 1 according to this third embodiment provides desirable effects similar to the discussed above.

As an alternative to the embodiment illustrated in FIG. 3, the inclination angle of the annular member 5 may gradually decrease along the proximal direction.

In addition, the third embodiment can be applied also to the second embodiment. The features of the third embodiment can also be applied to the fourth embodiment described below and illustrated in FIG. 4 which is a longitudinal cross-sectional view of the fourth embodiment of the guide wire.

Figure 4:
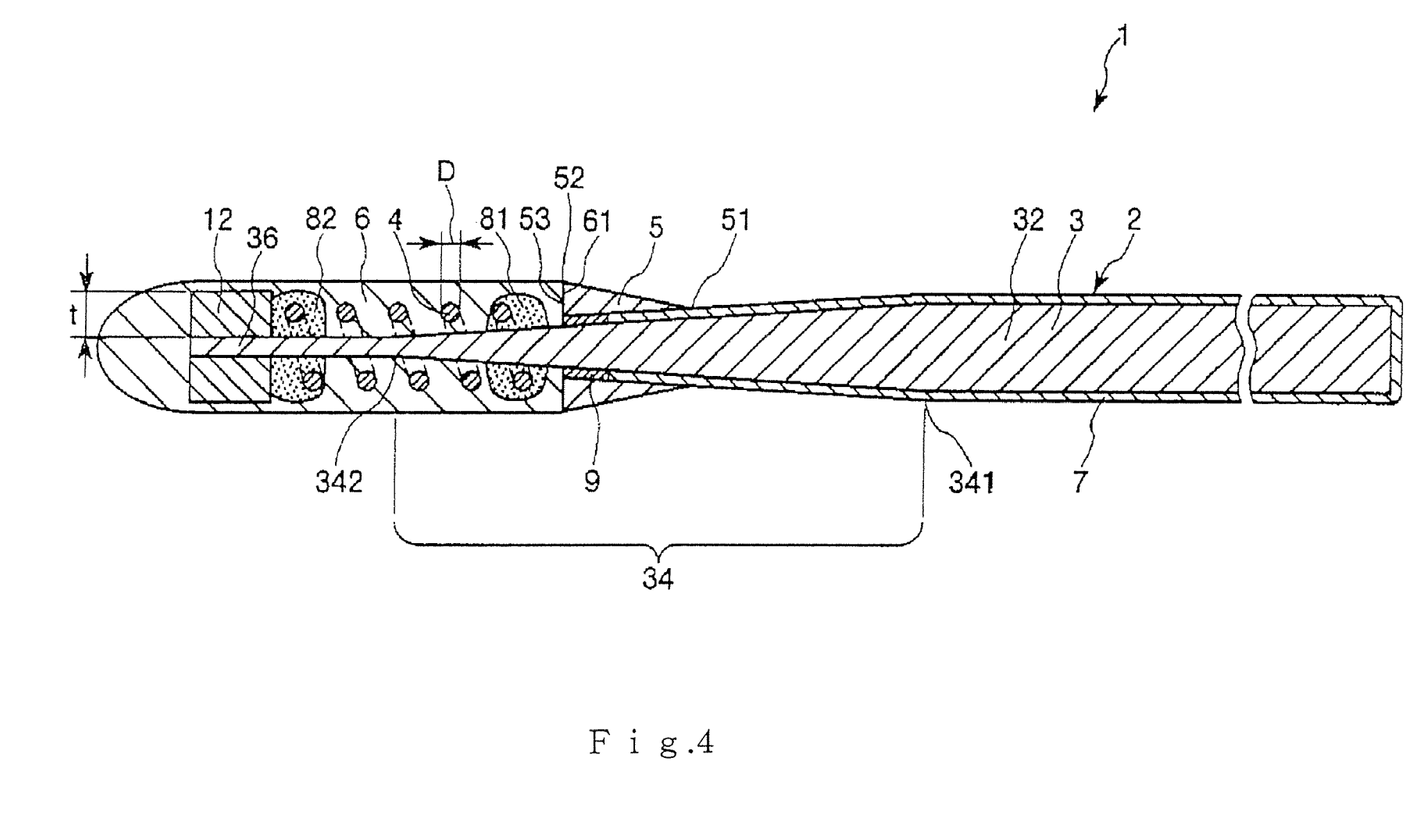
FIG. 4 is a longitudinal cross-sectional view of a fourth embodiment of the guide wire.

FIG. 4 illustrates a guide wire according to a fourth embodiment. The following description centers primarily on the difference(s) between this fourth embodiment and the embodiments described above. Features associated with this embodiment of the guide wire that are the same as those associated with embodiments described above are identified by common reference numerals, and a detailed description of such features is not repeated.

Referring to FIG. 4, the guide wire 1 according to the fourth embodiment has a tubular marker 12 made of or including a radiopaque material. In the illustrated embodiment, the marker 12 is cylindrical in shape. The marker 12 is disposed on the outer periphery of a distal section of a core wire 3, on the distal side of the coil 4. The outer periphery of the marker 12 is covered with the resin coating layer 6. In the illustrated embodiment, the distalmost end of the marker 12 is flush with the distalmost end of the core wire 3.

The material constituting the marker 12 is not particularly limited insofar as it is a radiopaque material. Examples of materials which can be used here include noble metals such as gold, platinum and tungsten and their alloys (e.g., platinum-iridium alloy).

It is preferable that $t \geq 1.25D$, more preferably $3.0D \geq t \geq 1.5D$, and further preferably $2.5D \geq t \geq 1.75D$, where t is the material thickness of the marker 12, and D is the outer diameter, in cross-section, of the filament forming the coil 4. This contributes to ensuring that the marker 12 is visible in an emphasized manner, as compared to the coil 4, under radioscopic observation, whereby the visibility of the marker 12 from the coil 4 can be set as demanded sufficiently.

The guide wire 1 according to this fourth embodiment provides desirable results similar to the discussed above.

The marker 12 desirably allows the position of the distal-most part of the guide wire 1 to be confirmed more easily and assuredly under radioscopic observation by the guide wire 1.

The aspects of the fourth embodiment of the guide wire can be applied also to the second embodiment of the guide wire and the third embodiment of the guide wire.

Figure 5:
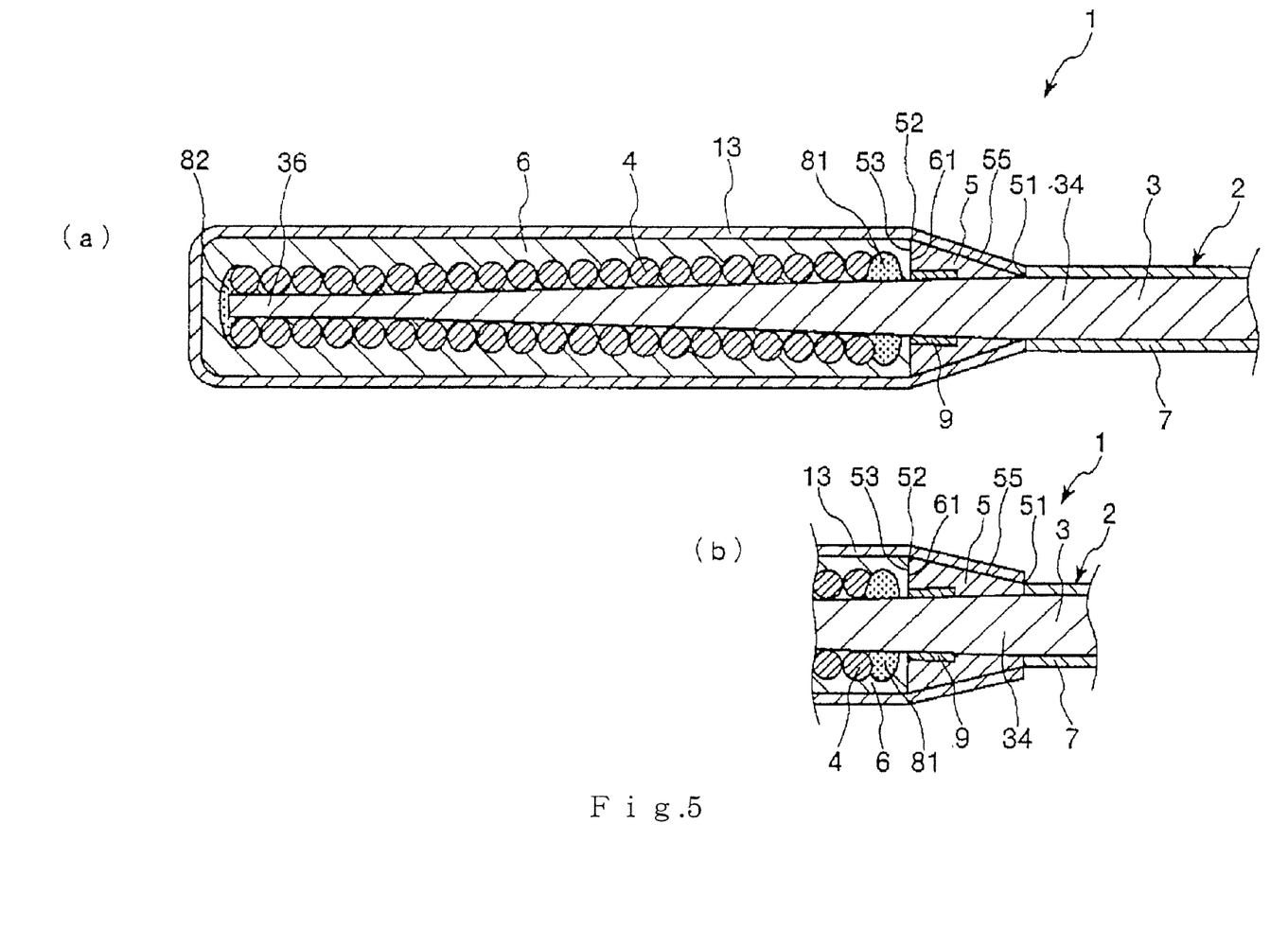

FIGS. 5(a) and 5(b) illustrate a fifth embodiment of the guide wire disclosed here, wherein FIGS. 5(a) and 5(b) show different versions of the guide wire. The following description of the guide wires shown in FIGS. 5(a) and 5(b) centers primarily on the difference(s) between this fourth embodiment and the embodiments described above. Features associated with this embodiment of the guide wire that are the same as those associated with embodiments described above are identified by common reference numerals, and a detailed description of such features is not repeated.

As shown in FIG. 5(a), the coil 4 of the guide wire 1 is configured as a so-called tight winding in which the adjacent turns of the filament forming the coil 4 contact each other. Namely, the filament is wound tightly so that the adjacent turns of the filament make contact with each other. Compressive forces pressing the turns of the filament against one another in the axial direction of the wire body 2 are generated in the natural condition. The term "natural condition" means a condition where no external force is being exerted or applied. Naturally, the compressive forces may not necessarily be generated in the natural condition.

As has been described in the first embodiment, where the coil 4 includes a radiopaque material, the guide wire 1 acquires a radioscopically visible property, which makes it possible to insert the guide wire 1 into a living body while checking the position of the distal part of the guide wire 1 under radioscopic observation. In this case, the tight winding provides easier confirmation of the position of the distal part under radioscopic observation.

In addition, the coil 4 is wound so that the filament makes contact with the outer periphery of a core wire 3. Namely, the inside surface of the coil 4 is in contact with the outer periphery of the core wire 3. This helps make it possible for the outer diameter of the distal section of the guide wire 1 to be made smaller, as compared with the case where the filament of the coil 4 is spaced from the outer periphery of the core wire 3. In addition, since the filament of the coil 4 is in contact with the outer periphery of the core wire 3, the coil 4 is inhibited or prevented from coming out of position relative to the core wire 3 at the time of manufacturing the guide wire 1, and so the guide wire 1 can be manufactured more easily.

The annular member 5 is provided around the outer periphery of the core wire 3, and the distal end of a coating layer 7 is located at the proximal end 51 of the annular member 5.

The outer surface of at least the distal section of the guide wire 1 is preferably covered with a hydrophilic lubricating layer 13 including a hydrophilic material. In this embodiment, the outer surface of the guide wire 1 in the region ranging from the distal end of the guide wire 1 to the proximal end 51 of the annular member 5, i.e., the outer surface of the resin coating layer 6 and the outer surface 55 of the annular member 5, are covered with the hydrophilic lubricating layer 13. This helps ensure that the hydrophilic material generates lubricity when wetted, whereby friction on the guide wire 1 is reduced, and slidability of the guide wire 1 is enhanced. Therefore, operational characteristics of the guide wire 1 are enhanced.

Particularly, a smooth under layer (not shown) is preferably provided on the outer surface 55 of the annular member 5, specifically, between the annular member 5 and the hydrophilic lubricating layer 13, whereby the slidability of the hydrophilic lubricating layer 13 at the outer surface 55 of the annular member 5 can be enhanced. Where the annular member 5 includes a metallic material, minute ruggedness of the outer surface 55 is liable to cause a lowering in the slidability intrinsic to the hydrophilic lubricating layer 13. In addition, since the outer surface 55 is inclined, it is liable to be caught by the distal end of a catheter or the like at the time of pulling out the guide wire 1. In view of this, the outer surface 55 of the annular member 5 is covered with the under layer to form a smooth surface, and the outer surface of the under layer is covered with the hydrophilic lubricating layer 13, whereby the slidability intrinsic of the hydrophilic lubricating layer 13 can be retained. As a result, the hydrophilic lubricating layer 13 at the portion of the outer surface 55 of the annular member 5 can also exhibit substantially the same slidability as that of the hydrophilic lubricating layer 13 at the portion of the outer surface of the resin coating layer 6. To form the under layer, diamond-like carbon can be used, as an example. The coefficient of friction of the under layer is preferably lower than that of the resin coating layer 6.

Examples of the hydrophilic material include cellulose-based polymeric materials, polyethylene oxide-based polymeric materials, maleic anhydride-based polymeric materials (for example, maleic anhydride copolymers such as methyl vinyl ether-maleic anhydride copolymer), acrylamide-based polymeric materials (for example, polyacrylamide, polyglycidyl methacrylate-dimethylacrylamide (PGMA-DMAA) block copolymer), water-soluble nylon, polyvinyl alcohol, and polyvinyl pyrrolidone.

Such hydrophilic materials, in many cases, exhibit lubricity when wetted upon water absorption, thereby reducing the frictional resistance between the guide wire 1 and the inside wall of a catheter used together with the guide wire 1. Consequently, the slidability of the guide wire 1 is enhanced, and the operationality of the guide wire 1 in the catheter is enhanced more.

Here, in the configuration shown in FIG. 5(a), the outer diameter of the proximal end 51 of the annular member 5 is equal (inclusive of approximately equal) to the outer diameter of the core wire 3 at the proximal end 51 of the annular member 5. In other words, a stepless continuous surface exists between the core wire 3 and the proximal end 51 of the annular member 5.

The outer diameter of the proximal end of the hydrophilic lubricating layer 13 is equal (inclusive of approximately equal) to the outer diameter of the distal end of the coating layer 7. In other words, a stepless continuous surface exists between the coating layer 7 and the hydrophilic lubricating layer 13.

In addition, in the configuration shown in FIG. 5(b), the outer diameter of the proximal end 51 of the annular member 5 is equal (inclusive of approximately equal) to the outer diameter of the distal end of the coating layer 7. In other words, a stepless continuous surface is formed between the coating layer 7 and the proximal end 51 of the annular member 5.

These versions of the guide wire 1, provide the same effects as those of the first embodiment described above.

The aspects of the guide wire shown in the fifth embodiment(s) of FIGS. 5(a) and 5(b) can be applied also to the second embodiment, the third embodiment and the fourth embodiment described above.

Figure 6:
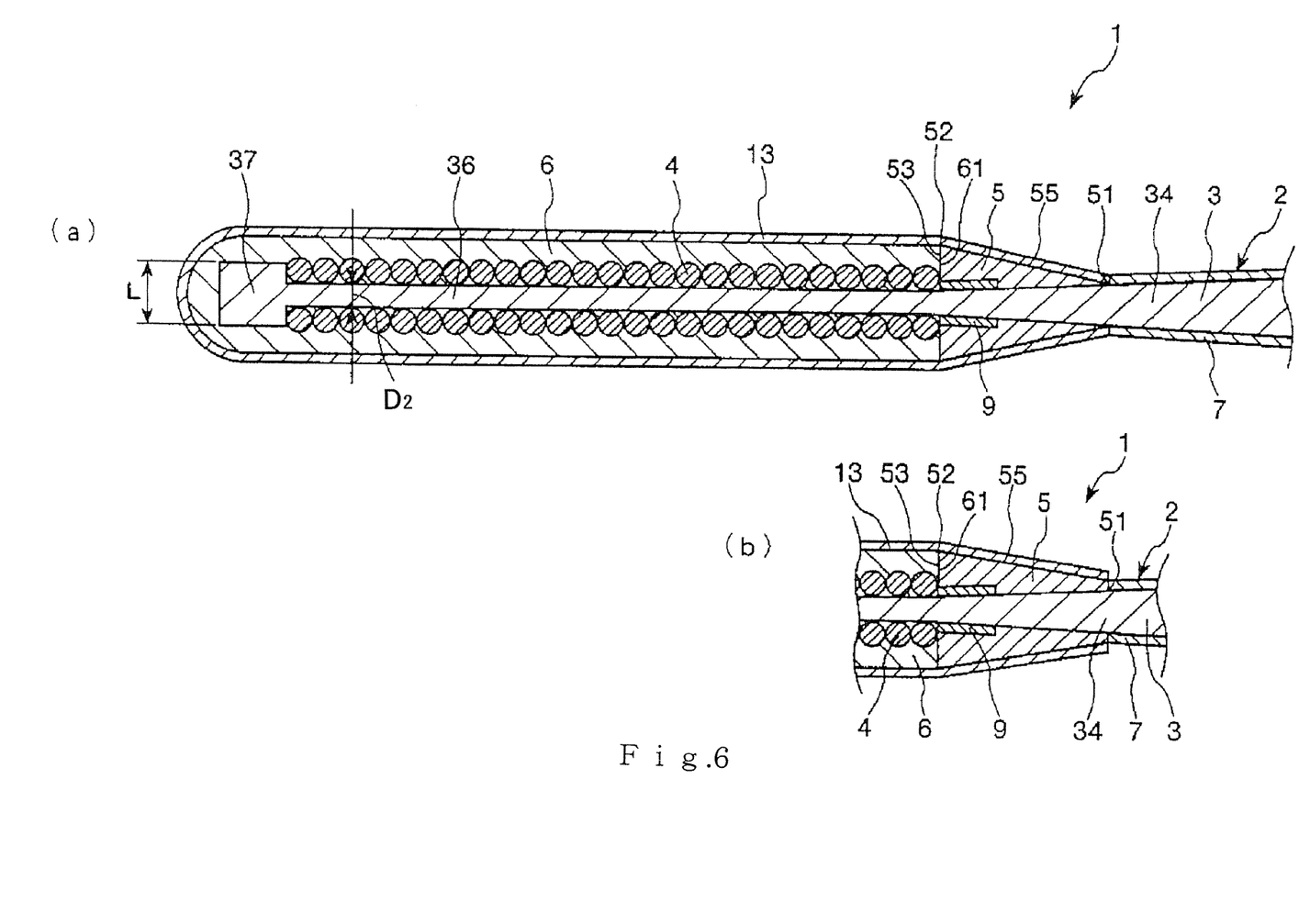

FIGS. 6(a) and 6(b) illustrate a sixth embodiment of the guide wire disclosed here, wherein FIGS. 6(a) and 6(b) show different versions of the guide wire.

The following description of the guide wires shown in FIGS. 6(a) and 6(b) centers primarily on the difference(s) between this fourth embodiment and the embodiments described above. Features associated with this embodiment of the guide wire that are the same as those associated with embodiments described above are identified by common reference numerals, and a detailed description of such features is not repeated.

As illustrated, the distalmost part of the core wire 3 has a flat shape. Specifically, the core 3 is provided at the distal end of a small diameter section 36 thereof with a flat section 37 having a flat shape. In the illustrated configuration, the flat section 37 has a substantially tetragonal flat plate-like shape, possessing a width greater than its thickness.

The width L, which is the dimension of the flat section in the radial direction of the coil 4, is greater than the inner diameter a of the coil 4. The width L of the flat section 37 may be set to be greater than the outer diameter D2 of the small diameter section 36. The flat section 37 is located on the distal side relative to a distal section of the coil 4. Specifically, the coil 4 is disposed between the flat section 37 and the annular member 5. The distal section of the coil 4 abuts on the flat section 37. The distal section of the coil 4 preferably is engaged with the flat section 37. The proximal section of the coil 4 abuts on the distal end face 53 of the annular member 5.

This makes it possible to inhibit or prevent the coil 4 from coming off from the distal end of the core wire 3. Consequently, it is possible to omit a fixing material for firmly attaching the coil 4 to the core wire 3. Naturally, the coil 4 may be fixed to the core wire 3 by a fixing material.

An outer layer (not shown) including a radiopaque material, for example, a noble metal such as gold, platinum and tungsten or an alloy containing the same (e.g., platinum-iridium alloy) may be provided on an outer surface of the flat section 37. This helps ensure that the position of the distal-most part of the guide wire 1 can be confirmed easily and assuredly under radioscopic observation.

The flat section 37 can be formed, for example, by press forming or the like. Specifically, for example, the length of the small diameter section 36 of the core wire 3 is set to include a portion corresponding to the flat section 37, and the distal-most section of the core wire 3 is subjected to press forming. As a result, the flat section 37 is formed at the distal end of the small diameter section 36.

According to this embodiment(s) of the guide wire 1, the same effects as those of the above-described fifth embodiment can be obtained.

The aspects of the guide wire shown in this sixth embodiment can be applied also to the first, second, third and fourth embodiments.

Figure 7:
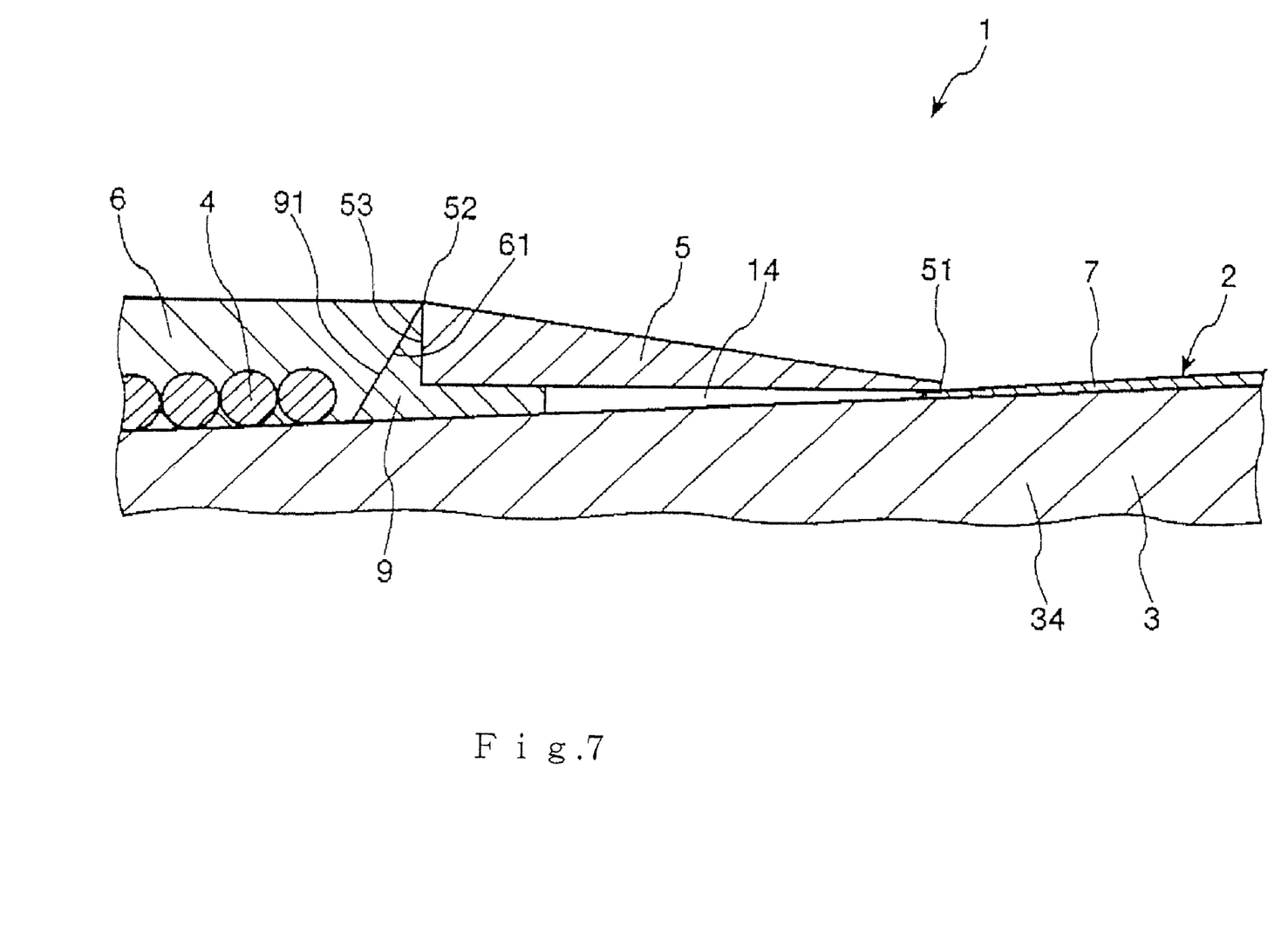
FIG. 7 is an enlarged longitudinal cross-sectional view of a portion of a guide wire according to a third embodiment.

FIG. 7 is a longitudinal cross-sectional view of a portion of a seventh embodiment of the guide wire disclosed here.

The following description centers primarily on the difference(s) between this seventh embodiment of the guide wire and the embodiments described above. Features associated with this seventh embodiment of the guide wire that are the same as those associated with embodiments described above are identified by common reference numerals, and a detailed description of such features is not repeated.

As shown in FIG. 7, in the guide wire 1 according to the seventh embodiment, the inner diameter of the proximal end 51 of the annular member 5 is equal (inclusive of approximately equal) to the inner diameter of the distal end 52 of the annular member 5. Specifically, the inner diameter of the annular member 5 is uniform (inclusive of substantially uniform) over its entire length from the proximal end 51 to the distal end 52.

A fixing material 9 is provided to fill a part of the space formed between the annular member 5 and the core wire 3, and to cover at least a part of the distal end face 53 of the annular member 5. In the illustrated embodiment, the fixing material 9 fills a distal-side part of the space between the annular member 5 and the core wire 3, and entirely covers the distal end face 53 of the annular member 5, with a gap 14 being left between the annular member 5 and the core wire 3.

In the longitudinal cross-sectional view shown in FIG. 7, the distal end face 91 of the fixing material 9 is inclined toward the distal side, and correspondingly the proximal end face 61 of the resin coating layer 6 is also inclined, and the distal end face 91 of the fixing material 9 and the proximal end face 61 of the resin coating layer 6 are in secure contact with each other. In other words, the distal end face 53 of the annular member 5 is joined to the proximal end face 61 of the resin coating layer 6 through the fixing material 9.

The fixing material 9 is preferably a resin fixing material, i.e., an adhesive. This helps ensure that the adhesion between the fixing material 9 and the resin coating layer 6 is enhanced, and exfoliation of the resin coating layer 6 is restrained.

The method for manufacturing the guide wire 1 is limited to a particular method. As an example, a manufacturing method may be adopted in which the fixing material 9 is applied to a distal-side part of the space between the annular member 5 and the core wire 3 and to the distal end face 53 of the annular member 5, then the annular member 5 is fixed to the core wire 3, and thereafter the coil 4 and the resin coating layer 6 are provided.

The aspects of the guide wire according to this seventh embodiment can be applied to the first to sixth embodiments.

While the guide wire according to the present invention has been described above based on the embodiments shown in the drawing figures, the invention is not limited to the disclosed and illustrated embodiments. The configurations of the individual components or parts may be replaced by alternative configurations having the same, similar or equivalent functional attributes. Also, features or components beyond those described above can be added.

Furthermore, the guide wires disclosed here can include combinations of two or more configurations (features) of the above-described embodiments.

The principles, embodiments, operational characteristics and the like of the guide wire have been described in the foregoing specification, but the invention which is intended to be protected is not to be construed as limited to the particular embodiments disclosed. The embodiments described herein are to be regarded as illustrative rather than restrictive. Variations and changes may be made by others, and equivalents employed, without departing from the spirit of the present invention. Accordingly, it is expressly intended that all such variations, changes and equivalents which fall within the spirit and scope of the present invention as defined in the claims, be embraced thereby.

What is claimed is:

1. A guide wire comprising:
a core wire comprising a distal end section and a proximal end section, a portion of the core wire between the distal end section and the proximal end section being a tapered section in which an outer diameter of the tapered portion varies and is reduced at a distal part of the tapered portion as compared to a proximal part of the tapered portion;
a resin coating layer covering an outer periphery of the distal end section of the core wire;
an annular member encircling at least a portion of the tapered section and positioned entirely on a proximal side of the resin coating layer;
the tapered section of the core wire extending distally beyond a distal end of the annular member;
the tapered section of the core wire extending proximally beyond a proximal end of the annular member;
the annular member being separate from the resin coating layer and possessing a distalmost end face joined to a proximalmost end face of the resin coating layer;
the annular member possessing a thickness that varies along its longitudinal extent, with the thickness of the annular member being less at its proximal end than at its distal end; and
the outer diameter of the distal end of the annular member being equal to the outer diameter of the proximal end of the resin coating layer.

2. The guide wire as set forth in claim 1, further comprising a coil encircling a portion of the distal section of the core wire and a portion of the tapered section of the core wire, the coil being covered by the resin coating layer and possessing a proximal-most end that is spaced in a distal direction from a distal-most end of the annular member.

3. The guide wire as set forth in claim 1, further comprising a coil encircling a portion or the distal section of the core wire and a portion of the tapered section of the core wire, the coil possessing a proximal end portion that is fixed to the core wire by a fixing material, the fixing material being spaced in a distal direction from a distal-most end of the annular member.

4. The guide wire as set forth in claim 1, further comprising a coil encircling a portion of the distal section of the core wire and a portion of the tapered section of the core wire, the coil being embedded in its entirety in the resin coating layer and being fixed in place to the core wire at least at two spaced apart locations by fixing members, one of the fixing members being located at a proximal-most end of the coil to fix the proximal-most end of the coil to the core wire.

5. The guide wire as set forth in claim 4, further comprising a coating layer covering the outer periphery of the proximal section of the core wire and the outer periphery of a part of the tapered section of the core wire, the annular member and the coating layer axially overlapping one another, with the annular member covering at least a part of an outer periphery of the coating layer.

6. The guide wire as set forth in claim 5, further comprising a fixing material fixing the annular member to the core wire, the fixing material and the annular member being different from one another.

7. The guide wire as set forth in claim 1, wherein the resin coating layer possesses a proximal end face from which axially extends a protrusion, and the annular member possesses a distal end face in which is formed an axially extending recess, the protrusion being positioned in the recess.

8. A guide wire comprising:
a wire body having a core wire;
a resin coating layer covering an outer periphery of a distal section of the wire body;
the resin coating layer having a proximal end whose outer diameter is greater than an outer diameter of a portion of the wire body immediately adjoining the proximal end of the resin coating layer so that the outer diameter of the proximal end of the resin coating layer and the outer diameter of the portion of the wire body immediately adjoining the proximal end of the resin coating layer forms a step-shaped space;
an annular member positioned at a proximal side of the resin coating layer and filling up the step-shaped space;
wherein an outer diameter of a distal end of the annular member and an outer diameter of the proximal end of the resin coating layer are equal; and
a distal end face of the annular member is joined to a proximal end face of the resin coating layer.

9. The guide wire as set forth in claim 8, further comprising a helical coil covering the outer periphery of a portion of the wire body, the coil being covered by the resin coating layer, the coil possessing a proximal-most end that is spaced in a distal direction from a distal-most end of the annular member.

10. The guide wire as set forth in claim 8, wherein the outer diameter of the annular member gradually decreases from a distal side of the annular member toward a proximal side of the annular member.

11. The guide wire as set forth in claim 8, wherein a stepless continuous surface is formed between the wire body and a proximal end of the annular member.

12. The guide wire as set forth in claim 8, wherein the resin coating layer possesses a proximal end face from which extends a protrusion, and the annular member possesses a distal end face in which is formed a recess, the protrusion being positioned in the recess.

13. The guide wire as set forth in claim 8, wherein the annular member possesses a hardness greater than a hardness of the resin coating layer.

14. The guide wire as set forth in claim 8, wherein the annular member is comprised of a metal or a hard resin.

15. The guide wire as set forth in claim 8, further comprising a coil covering the outer periphery of the distal section of the wire body, the coil being comprised of a helically wound filament, the coil possessing an outer periphery entirely covered by the resin coating layer.

16. The guide wire as set forth in claim 15, wherein the coil comprises adjacent turns that contact each other.

17. The guide wire as set forth in claim 15, wherein the coil possesses an inner periphery in contact with an outer periphery of the wire body.

18. The guide wire as set forth in claim 15, wherein the core wire possesses a distal end portion configured as a flat section having a width greater than its thickness and larger than an inner diameter of the coil, the coil being disposed between the flat section and the annular member.

19. The guide wire as set forth in claim 8, wherein an outer surface of the resin coating layer is coated with a hydrophilic lubricating layer comprised of a hydrophilic material, the hydrophilic lubricating layer being positioned on a distal side relative to a proximal end of the annular member.

20. A guide wire comprising:

a wire;

a resin coating layer covering an outer periphery of a distal section of the wire;

an annular member covering the wire and provided on a proximal side of the resin coating layer;

the annular member having a distal end possessing an outer diameter;

the resin coating layer having a proximal end possessing an outer diameter;

the outer diameter of the distal end of the annular member and the outer diameter of the proximal end of the resin coating layer being equal, and a distal end face of the annular member being joined to a proximal end face of the resin coating layer;

the outer diameter of the annular member gradually decreasing from a distal side of the annular member toward a proximal side of the annular member;

a distal stepless continuous surface exists between the distal end of the annular member and the proximal end of the resin coating layer;

a proximal stepless continuous surface exists between the wire and the proximal end of the annular member; and a hydrophilic lubricating layer covering an outer surface of the resin coating layer and an outer surface of the annular member, and terminating at a proximal end of the annular member.

21. The guide wire as set forth in claim 20, further comprising a helical coil covering the outer periphery of a portion of the wire body, the coil being covered by the resin coating layer, the coil possessing a proximal-most end that is spaced in a distal direction from a distal-most end of the annular member.

22. The guide wire as set forth in claim 20, further comprising a coil covering an outer periphery of a distal section of the wire body, the coil being comprised of a helically wound filament, the coil possessing an outer periphery entirely covered by the resin coating layer.

23. The guide wire as set forth in claim 22, wherein the core wire possesses a distal end portion configured as a flat section having a width greater than its thickness and larger than an inner diameter of the coil, the coil being disposed between the flat section and the annular member.

24. The guide wire as set forth in claim 23, wherein a distalmost end of the coil abuts the flat section of the core wire.

\* \* \* \* \*